(12) United States Patent
Thöing

(10) Patent No.: US 7,188,834 B2
(45) Date of Patent: Mar. 13, 2007

(54) GROUPING OF FILM-LIKE OR SHEET-LIKE MATERIALS

(75) Inventor: Heinrich Thöing, Bad Neuenahr-Ahrweiler (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 58 days.

(21) Appl. No.: 10/476,815

(22) PCT Filed: Apr. 16, 2002

(86) PCT No.: PCT/EP02/04179

§ 371 (c)(1),
(2), (4) Date: Apr. 14, 2006

(87) PCT Pub. No.: WO02/089716

PCT Pub. Date: Nov. 14, 2002

(65) Prior Publication Data

US 2004/0140236 A1    Jul. 22, 2004

(30) Foreign Application Priority Data

May 5, 2001    (DE) ................. 101 21 971

(51) Int. Cl.
*B65H 3/08* (2006.01)
(52) U.S. Cl. .......... 271/103; 271/93; 271/90; 271/3.11; 428/138
(58) Field of Classification Search ......... 271/90, 271/93, 96, 103, 108, 3.11; 428/138
See application file for complete search history.

(56) References Cited

U.S. PATENT DOCUMENTS 2,298,363 A    10/1942 Gans
3,965,906 A  *  6/1976 Karami ............... 604/366
RE30,424 E   * 11/1980 Heldenbrand ......... 119/170
4,567,081 A  *  1/1986 VanHorne ............ 428/138

(Continued)

FOREIGN PATENT DOCUMENTS

| DE | 1 956 948 | 6/1970 |
| DE | 38 11 634 A1 | 10/1989 |
| DE | WO 94/06419 | 3/1994 |
| DE | 44 00 713 A1 | 7/1995 |

(Continued)

OTHER PUBLICATIONS

IWKA Packaging sheet for Three and Four Side Sealed Bags (English/German)—http://iwka-pacunion.de/packmittel/Prim/printversion_sachet_en.html).

*Primary Examiner*—Patrick Mackey
(74) *Attorney, Agent, or Firm*—Frommer Lawrence & Haug LLP

(57) ABSTRACT

The invention relates to a method for grouping a multitude of film-like or sheet-like materials, which are stacked in a magazine (20) and which consist of at least one material layer, using at least one suction apparatus (42), which suctions the film-like or sheet-like materials in a clocked matter while removing them from the magazine, whereby one film-like or sheet-like material at a time directly rests with a portion of its surface that forms a contact surface against the suction device. To this end, one portion of the magazine contents consists of gas-impermeable film-like or sheet-like materials whereas another portion contains film-like or sheet-like materials that are each provided with at least one gas-permeable zone. The invention develops a method for grouping film-like or sheet-like materials during which a number of film-like or sheet-like materials can be grouped without impairing the speed of subsequent processing.

11 Claims, 3 Drawing Sheets

U.S. PATENT DOCUMENTS

| | | | |
|---|---|---|---|
| 4,780,352 A * | 10/1988 | Palumbo | 428/138 |
| 4,925,453 A * | 5/1990 | Kannankeril | 604/378 |
| 5,569,484 A | 10/1996 | Muller et al. | |
| 5,702,798 A * | 12/1997 | Sugita et al. | 428/131 |
| 5,941,681 A | 8/1999 | Piotrowski et al. | |

FOREIGN PATENT DOCUMENTS

| | | |
|---|---|---|
| DE | 44 40 727 A1 | 5/1996 |
| DE | 198 07 970 C1 | 4/1999 |
| GB | 843631 | 11/1956 |

* cited by examiner

GROUPING OF FILM-LIKE OR SHEET-LIKE MATERIALS

DESCRIPTION

The invention relates to a method for grouping a multiplicity of film-like or sheet-like materials which are stacked in a magazine and which consist of at least one material layer, using at least one suction apparatus which suctions the film-like or sheet-like materials in a clocked-manner and removes them from the magazine, one film-like or sheet-like material in each case resting directly with a portion of its surface, forming a contact surface, against the suction device.

Methods for individually separating film-like or sheet-like materials stacked in a magazine are known. In these methods, the individual film-like or sheet-like material is removed from the magazine in a clocked manner by a suction apparatus and is passed onward individually for further processing.

If a plurality of film-like or sheet-like materials are to be further processed simultaneously, this requires a plurality of magazines, for example, in which the different film-like or sheet-like materials are stored. This is costly and reduces the speed of the further processing.

The present invention is therefore based on the problem of developing an operating method for grouping film-like or sheet-like materials in which a variable number of film-like or sheet-like materials can be grouped without adversely affecting the speed of the further processing.

This problem is solved by the features of the main claim. To this end, one portion of the magazine content consists of gas-impermeable film-like or sheet-like materials, while another portion contains film-like or sheet-like materials each provided with at least one gas-permeable zone. In the magazine, at least one gas-permeable film-like or sheet-like material is followed by a gas-impermeable film-like or sheet-like material. In addition, during the suctioning of the film-like or sheet-like materials by the suction apparatus, one gas-permeable film-like or sheet-like material lies with its gas-permeable zone directly on the suction apparatus, and the suction apparatus takes up the next farthest away stacked gas-impermeable film-like or sheet-like material.

In the removal from the magazine, a plurality of film-like or sheet-like materials can be removed jointly by the suction apparatus and passed onward for further processing. For example, it is possible to remove one gas-permeable and one gas-impermeable film-like or sheet-like material from the magazine, or for example two or more gas-permeable film-like or sheet-like materials and one gas-impermeable film-like or sheet-like material. The gas-impermeable film-like or sheet-like material always forms the last film-like or sheet-like material removed in a cycle. The film-like or sheet-like material here called gas-impermeable can, at least within certain limits, be gas-permeable, in which case the gas stream developing in this part during suctioning is considerably smaller than the gas stream which develops upon suctioning of the film-like or sheet-like material here called gas-permeable.

The film-like or sheet-like materials removed in this way can be passed on jointly for further processing. The downstream work steps do not have to wait for a batch to be assembled. Thus, the speed of the further processing is not adversely affected by the number of film-like or sheet-like materials being further processed jointly.

In a subsequent work step, the film-like or sheet-like materials are then conveyed for example to a packaging unit. The two or more film-like or sheet-like materials removed from the magazine in one cycle are then packaged in this packaging unit. The material can for example be formed as a single layer or can be made up of several layers placed one on top of the other. At least one of the film-like or sheet-like materials packaged in a packaging unit contains a gas-permeable zone. In at least one other film-like or sheet-like material, the gas permeability is at most 50% of the above-mentioned gas permeability. The last-mentioned film-like or sheet-like material can also be designed with no gas permeability.

Further details of the invention will become evident from the dependent claims and from the following description of an illustrative embodiment which is shown diagrammatically.

Figure 3:
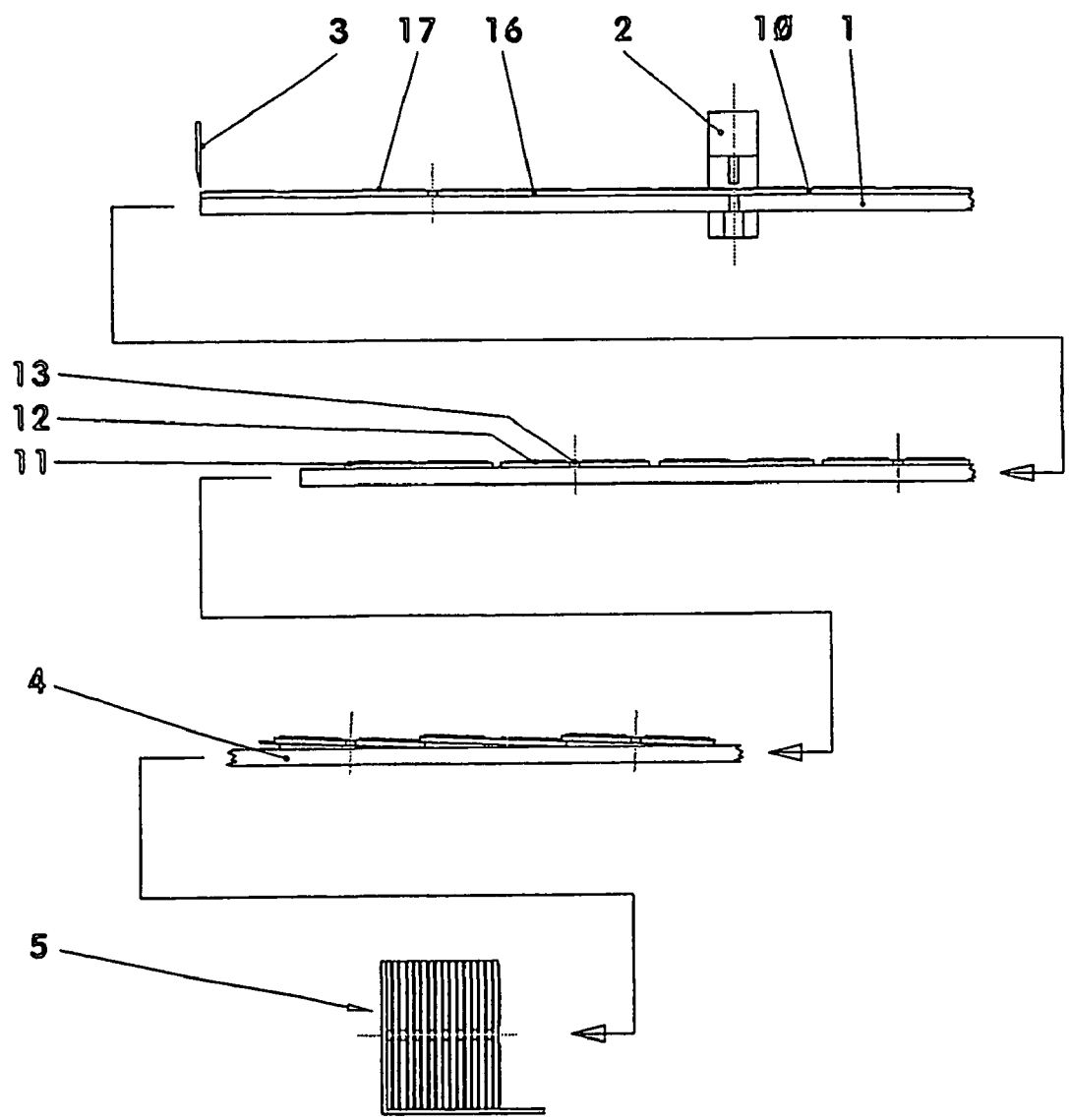
FIG. 3 shows a side view of the delivery of the film-like or sheet-like materials to a magazine via several work stations.
Figure 4:
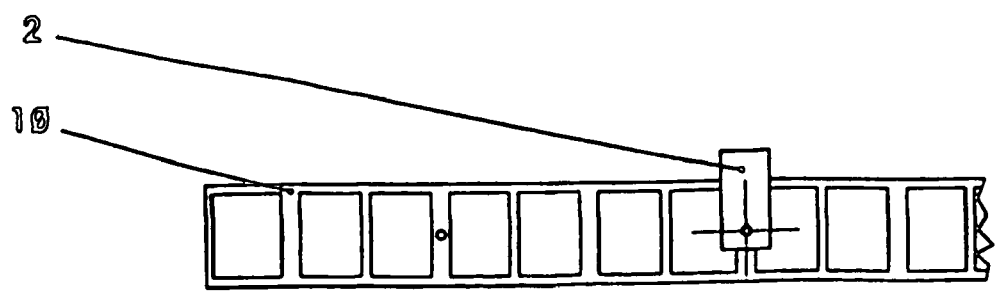
FIG. 4 shows a plan view of FIG. 3.

FIGS. 3 and 4 show the grouped separation, working and delivery of film-like or sheet-like materials (11, 12) to a magazine (5, 20). Since they are mostly multi-layered, these materials are referred to below as composite material films (11, 12). With the aid of a conveyor device (1), a composite material film web (10) is delivered to a hole puncher (2) and to a cutting device (3). At the cutting device (3), individual composite material films (11, 12) generally of identical length are cut off from the composite material film web (10), and they are delivered, overlapping, to a stream feeder (4). The composite material films (11, 12) are now delivered, in a stacked formation, to the magazine (20) shown in FIG. 1, either via a storage magazine (5) or directly.

The composite material film web (10), for example a plaster web, comprises a protective film (16), for example a plaster support, and, adhering to the latter and coated on one side, active-substance supports (17), for example in the form of plasters. The plaster web (10) in this case has, for example, the width of one plaster (17).

The plasters (17) are used, for example, as therapeutic systems for transferring active substances to a patient's skin. They are, for example, rectangular, elliptic, round, etc. On their outer face they have a layer of support material which is impermeable to the active substance. On their coated side, for example at the center thereof, they are provided with a reservoir of nonwoven fabric or foam, for example of cotton, cellulose, polyethylene, polyurethane, etc., to take up active substance, for example solutions, emulsions or suspensions. At the outer edges of the plasters (17), the layer of support material is provided with an adhesive layer at least in some areas on the coated side.

The plasters (17) can, for example, also be matrix systems based on mixtures of synthetic resins, elastomers and softeners or natural proteins, polysaccharides or disaccharides, synthetic water absorbers, moisture-retaining agents and, if appropriate, natural adhesives.

In the various embodiments of the plasters (17), it is also possible to incorporate elements for controlling the delivery of substances to a patient's skin and for separating individual active-substance layers. The support film can also be breathable and vapor-permeable.

The plaster support (16) is, for example, a protective film that is impermeable to active substance. It can, for example, be made of paper, of polymer film, of aluminum-coated plastic film, etc. The plaster support (16) adheres releasably to the plaster (17) and is removed from the latter before the therapeutic system (17) is applied. It gives the plaster (17) rigidity prior to use and prevents escape of active substances from the plaster (17).

For punching and, for example, separating the plasters (17) into groups, the plaster web (10) is conveyed by the conveyor device (1) in the direction of the cutting device (3) until it extends beyond the latter by a predetermined extend, for example the length of two plasters (17). During the cutting of plaster strips (11, 12) from the plaster web (10), a hole puncher (2) is activated upon each second cut, which hole puncher (2) for example produces an interruption (13) in the plaster support (16) between two plasters (17). After each cut, the plaster web (10) is advanced, and further plaster strips (11, 12) are cut off.

Since the interruption (13) is produced only during every second cut by the cutting device (3), in the illustrative embodiment only every second cut-off plaster strip (12) has an interruption (13). The shape of the interruption (13) can be round, square, elliptic, etc. It can also be made up of one or more gas-permeable zones (13) which are likewise arranged approximately centrally and/or in the zone between the plasters (17) on the plaster strip (12).

With a suitable relationship between the cuts by the cutting device (3) and the working strokes of the hole puncher (2), the number of holed plaster strips (12) to the number of unholed plaster strips (11) can be varied. If, for example, during three successive cuts by the cutting device (3), the hole puncher (2) executes working strokes only during the first two, two holed plaster strips (12) are followed by an unholed plaster strip (11).

On the stream feeder (4), the individual plaster strips (11, 12), shown in cross section, are stacked, in the order in which they were cut off, so that the plaster strips (11, 12) lie one on top of another. Here, therefore, an unholed plaster strip (11) lies on each holed plaster strip (12). The stacked plaster strips (11, 12) can then be delivered to one of the magazines (5, 20) for further processing, cf. FIG. 1.

Figure 1:
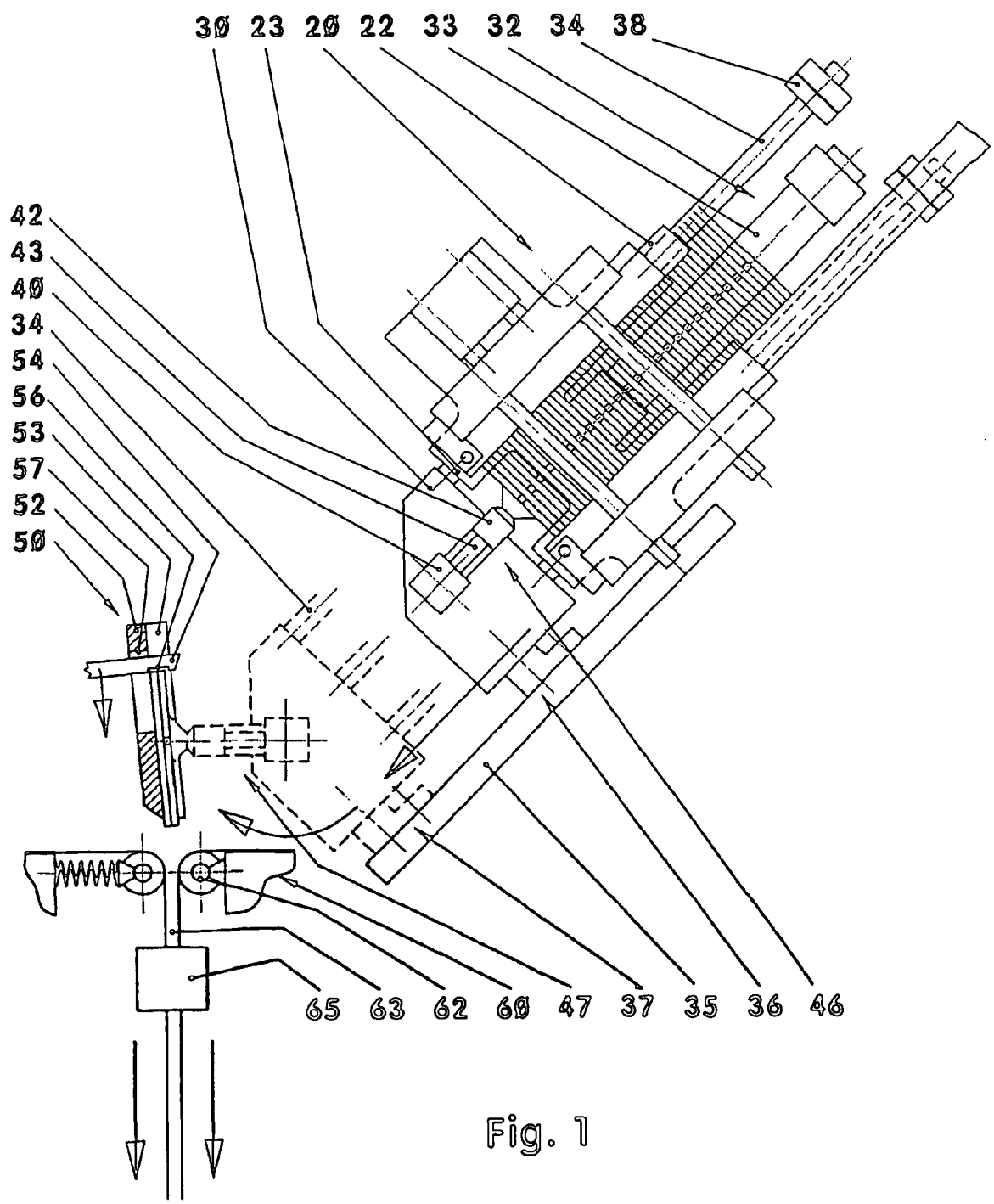
FIG. 1 shows a side view of the delivery of film-like or sheet-like materials from a magazine to a packaging machine.

FIG. 1 shows the transfer of plaster strips (11, 12) from the magazine (20) to a packaging machine (60). A flat suction apparatus (42) mounted pivotably on a carriage (30) bears on the lowermost of the plaster strips (11, 12) stacked in the magazine (20). This flat suction apparatus (42) removes plaster supports (11, 12) in bundles from the magazine (20).

The carriage (30) then moves the flat suction apparatus (42) together with the plaster strips (11, 12) to the feed unit (50) of a packaging machine (60). The plaster strips (11, 12) are packaged in the latter.

Figure 2:
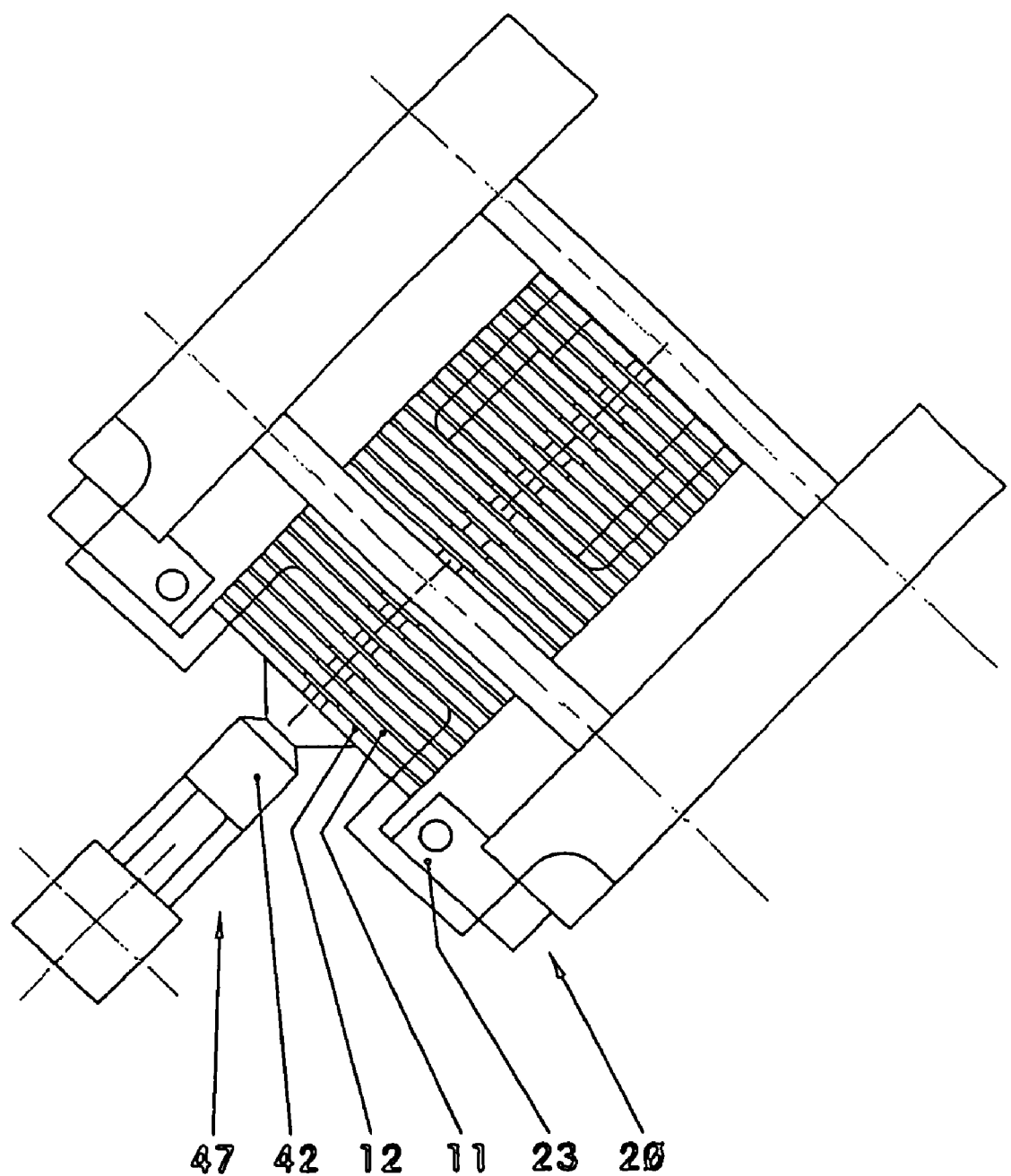
FIG. 2 shows a detail of the removal area of the magazine.

The magazine (20) is arranged, for example, at an angle of 45° to the vertical. In the magazine (20), cf. FIG. 2, the plaster strips (11, 12) are received and guided in receiving rails (22). The receiving rails (22) are, for example, U-shaped profiles which, at their lower end, are delimited at least partially by in each case one bearing piece (23).

The delivered plaster strips (11, 12) lie in the magazine (20) under the effect of gravity. The lowermost plaster strip (12) lies on the bearing pieces (23). The other delivered plaster strips (11, 12) then lie on this plaster strip (12).

The carriage (30) is arranged underneath the magazine (20) in a direction perpendicular to the stacked plaster strips (11, 12). It is secured on two mutually parallel guide bars (34) which are guided in the magazine (20), for example in ball-bearing bushes. Arranged underneath the carriage (30) there is a support guide (35) on which the magazine (20) is arranged. The carriage (30) is driven by a pneumatic cylinder/piston unit (32) which, for example, is arranged centrally between the guide bars (34). The cylinder (33) of the cylinder/piston unit (32) lies level with the magazine (20). In an upper end position (36) of the carriage (30), the piston of the cylinder/piston unit (32) is for example retracted, and, in a lower end position (37), the piston is extended for example.

The swivel head (40) is also activated pneumatically for example. It is mounted on the side of the carriage (30) for example. Its pivot axis lies transverse to the longitudinal direction of the cylinder/piston unit (32) and perpendicular to the plane of the drawing in FIG. 1. In the illustrative embodiment, the swivel head (40) covers a swivel angle of about 225°.

The flat suction apparatus (42) sits on the swivel head (40) and is pivoted by the latter. In a removal position (46), the center axis of the flat suction apparatus (42) lies in the stacking direction of the magazine (20) and perpendicular to the plane of the drawing in FIG. 1. If appropriate, the suction pressure of the flat suction apparatus (42) is variable.

In the transfer position (47), the center axis of the flat suction apparatus (42) is approximately horizontal and level with the center of the feed unit (50) to the packaging machine (60).

The feed unit (50) has an insert plate (52) with lateral guide edges (53), said insert plate (52) being arranged, for example, at an angle of 5° to the vertical. Two insert pins (54) guided in oblong holes (57) of the insert plate (52) are arranged for example at the upper end of the feed unit (50). In FIG. 1, only one of these insert pins (54) is shown.

In the removal position (46), the flat suction apparatus (42) lies centrally on the lowermost plaster strip (12) in the magazine (20). On switching on the flat suction apparatus (42), this plaster strip (12) is suctioned by the flat suction apparatus (42). In the suction zone in which the plaster strip (12) lies on the flat suction apparatus (42), this plaster strip (12) has an interruption (13) through which the vacuum generated by the flat suction apparatus (42) propagates to the next plaster strip (11), which has no interruption (13). Here, the suction stream of the flat suction apparatus is greater than the sum of all the leakage streams which may arise between the individual plaster strips (11, 12) involved. The air pressure acting on this gas-impermeable plaster strip (11) presses all the plaster strips (12) lying between the flat suction apparatus (42) and this plaster strip (11) as a bundle against the flat suction apparatus (42). If appropriate, the gas-impermeable plaster strips (11) can also be made gas-permeable within certain limits. The gas permeability of these plaster strips (11) is then, for example, so low that the gas stream developing, during suctioning by the flat suction apparatus (42), through the gas-impermeable plaster strip (11) is less than the gas stream through the gas-permeable plaster strip (12).

As the carriage (30) moves away in the direction of the feed unit (50), the vacuum on the flat suction apparatus (42) is maintained. The plaster strips (11, 12) are withdrawn from the magazine (20). In doing so, the outer ends of the plaster strips (11, 12) slide down from the bearing pieces (23). In the process, the plaster strips (11, 12) bulge elastically. As soon as the plaster strips (11, 12) have been removed from the magazine (20), the elastic deformation is reversed.

While the carriage (30) travels to its lower end position (37), the swivel head (40), together with the flat suction apparatus (42) and the plaster strips (11, 12) bearing on the latter, pivots in a clockwise direction toward the transfer position (47). Once the lower end position (37) of the carriage (30) and the transfer position (47) of the flat suction apparatus (42) have been reached, the plaster strips (11, 12) are transferred to the feed unit (50).

In doing so, the plaster strips (11, 12) are placed on the insert plate (52) of the feed unit (50) and are pushed upward along the latter.

With the plaster strips (11, 12) bearing on the insert plate (52), they adhere for example to the inclined insert plate (52). They are secured against lateral slipping by means of the guide edges (53).

In a subsequent work step, the suctioning function of the flat suction apparatus (42) is switched off. Directly thereafter, the plaster strips (11, 12) are moved downward in the direction of the packaging machine (60) with the aid of the insert pins (54).

Before and/or during the downward travel of the insert pins (54), the swivel head (40) pivots counterclockwise until the flat suction apparatus (42) again points in the direction of the magazine (20). Once the carriage (30) has traveled to the upper end position (36), the next plaster strips (11, 12) are removed from the magazine (20). If, for example, the two following plaster strips (12) are provided with an interruption (13) while the third strip (11) has no interruption (13), the suction effect through the two gas-permeable plaster strips (12) acts on the gas-impermeable, third plaster strip (11). All three strips are removed together and are delivered via the feed unit (50) to the packaging machine (60).

The packaging machine (60) comprises, for example, two rolls of film which, in the packaging area, are routed as webs of packaging material (63) on respective guide rollers (62). The two guide rollers (62) define a gap which, between the webs (63) of packaging material, is wider than the thickness of a standard bundle of plaster strips (11, 12). One of the guide rollers (62) is spring-mounted in an arrangement perpendicular to the gap, for example. The two webs (63) of packaging material each form an outer face of the package and, after the packaged material has been inserted, are welded to form side-sealed bags, peelable bags or tubular bags. A thickness gauge (65) then tests the thickness of the package.

However, on the packaging machine (60), the plaster strips (11, 12) can also be placed in thermoformed parts, for example.

The plaster strips (11, 12) to be packaged are introduced from the feed unit (50) down into between the webs (63) of packaging material in the area of the guide rollers (62). The two guide rollers (62) are at least partially pressed apart from one another in the process. After welding of the four-edge sealed bags, for example, the thickness of the individual four-edge sealed bags is determined using the thickness gauge (65). The thickness of the four-edge sealed bag is a measure of the number of plastic strips (11, 12) contained in the bag. Depending on the number of plaster strips (11, 12) in a bag, this bag can be passed onward to the appropriate further-processing station or to a rejection point. The filled four-edge sealed bags can thus be produced in an automated manner with a varying number of plaster strips (11, 12) per bag.

If appropriate, the method can also be used for the packaging of individual plaster strips (11). For this purpose, a large number of gas-impermeable plaster strips (11) lie on top of one another in the magazine (20). On the thickness gauge (65), too small a thickness of the four-edge sealed bags is then interpreted as an empty bag. The latter is then conveyed to the rejection point.

List of Reference Numbers:
1 conveyor device
2 hole puncher
3 cutting device
4 stream feeder
5 storage magazine
10 composite material film web, plaster web
11 film-like or sheet-like materials, gas-impermeable; composite material films, gas-impermeable; plaster strips, not holed
12 film-like or sheet-like materials, gas-permeable; composite material films, gas-permeable; plaster strips, holed
13 interruption in (12), gas-permeable zones in (12)
16 protective film, plaster support
17 active-substance support, plaster, therapeutic system
20 magazine
22 receiving rails
23 bearing pieces
30 carriage
32 cylinder/piston unit
33 cylinder
34 guide bars
35 support guide
36 upper end position
37 lower end position
38 abutments
40 swivel head
42 suction apparatus, flat suction apparatus
43 center axis
46 removal position
47 transfer position
50 feed unit
52 insert plate
53 guide edges
54 insert pins
56 cutout
57 oblong holes
60 packaging machine
62 guide rollers
63 webs of packaging material
65 thickness gauge

The invention claimed is:

1. A process for grouping a multiplicity of films or sheets consisting of the same material, having the same size and being gas-impermeable at the beginning of the process, which comprises:
   (a) providing at least every second of said films or sheets following on each other on a conveyer device with at least one gas-permeable zone,
   (b) conveying said films or sheets to a magazine,
   (c) stacking said films or sheets therein that way, that at least one film or sheet with at least one gas-permeable zone is followed by a film or sheet without any gas-permeable zone,
   (d) removing said films or sheets from said magazine by means of at least one suction apparatus in a clocked way, wherein one film or sheet having at least one gas-permeable zone lies with at least one gas-permeable zone directly on said suction apparatus,
   (e) attracting by suction through said gas-permeable zone of said film or sheet the next farthest away stacked film or sheet having no gas-permeable zone, and
   (f) removing at least one film or sheet having at least one gas-permeable zone together with a film or sheet having no gas-permeable zone as a bundle from said magazine.

2. The process as claimed in claim 1 wherein a gas-permeable zone is an interruption in the form of a large individual hole or represents a sum of several smaller holes, the cross-sectional area of the large individual hole being at least approximately equal to the cross-sectional area of the sum of all the smaller holes.

3. The process as claimed in claim 1 wherein the interruption is arranged near the center of the film or sheet material.

4. The process as claimed in claim 1 wherein the film or sheet materials are plaster strips.

5. The process as claimed in claim 1 wherein the plaster strips comprise several plasters.

6. The process of claim 5, wherein the several plasters contain an active substance and have (a) an outer face which is impermeable to the active substance; and (b) a coated side with a reservoir of non-woven fabric or foam.

7. The process of claim 5, wherein the several plasters contain a matrix system based on mixtures of synthetic resins, elastomers, softeners, natural proteins, polysaccharides or disaccharides, synthetic water absorbers, moisture-retaining agents and natural adhesives.

8. The process as claimed in claim 1 wherein the suction apparatus is a flat suction apparatus.

9. The process as claimed in claim 1 wherein the pressure of the suction apparatus is adjustable.

10. The process as claimed in claim 1 wherein a device for producing the interruptions is placed upstream of the magazine.

11. The process as claimed in claim 1 wherein a device for packaging the removed film or sheet materials is placed downstream of the magazine.

* * * * *